(12) United States Patent
Moszner et al.

(10) Patent No.: US 6,953,832 B2
(45) Date of Patent: Oct. 11, 2005

(54) DENTAL MATERIALS BASED ON POLYFUNCTIONAL AMIDES

(75) Inventors: Norbert Moszner, Eschen (DE); Frank Zeuner, Vaduz (DE); Volker Rheinberger, Vaduz (DE); Jörg Angermann, Feldkirch (AT); Thomas Völkel, Oberreitnau (DE)

(73) Assignee: Ivoclar Vivadent AG, Schaan (LI)

( * ) Notice: Subject to any disclaimer, the term of this patent is extended or adjusted under 35 U.S.C. 154(b) by 12 days.

(21) Appl. No.: 10/045,358

(22) Filed: Jan. 14, 2002

(65) Prior Publication Data

US 2002/0143138 A1 Oct. 3, 2002

Related U.S. Application Data

(60) Provisional application No. 60/289,097, filed on May 7, 2001.

(30) Foreign Application Priority Data

Jan. 15, 2001 (DE) .......................... 101 01 523

(51) Int. Cl.$^7$ ............................ A61K 6/08; C08K 5/00; C08J 3/00; C09K 3/00
(52) U.S. Cl. ..................... 528/310; 528/322; 523/115; 523/116; 523/118; 523/120; 106/35; 433/228.1; 524/521; 524/523; 525/328.2; 522/40; 522/46; 522/48; 522/84; 522/908
(58) Field of Search ............................ 528/310, 99, 282, 528/48; 523/115, 116, 118, 120; 106/35; 433/228.1; 522/40, 46, 48, 84, 908; 525/328.2; 524/521, 523

(56) References Cited

U.S. PATENT DOCUMENTS

| | | | |
|---|---|---|---|
| 1,039,750 A | | 8/1912 | Bruckmann |
| 3,660,343 A | | 5/1972 | Saffir |
| 3,926,870 A | | 12/1975 | Keegan et al. |
| 4,110,184 A | * | 8/1978 | Dart et al. ............... 522/18 |
| 4,707,504 A | | 11/1987 | Walkowiak et al. |
| 5,011,868 A | | 4/1991 | Keegan |
| 5,154,762 A | * | 10/1992 | Mitra et al. ............... 106/35 |
| 5,302,630 A | * | 4/1994 | Mukai et al. ............. 523/118 |
| 5,334,625 A | * | 8/1994 | Ibsen et al. ............. 523/115 |
| 5,539,017 A | * | 7/1996 | Rheinberger et al. ....... 523/116 |
| 5,560,749 A | | 10/1996 | Madison et al. |
| 5,922,786 A | | 7/1999 | Mitra et al. |
| 6,133,338 A | | 10/2000 | Kimura et al. |
| 6,255,360 B1 | * | 7/2001 | Domschke et al. ........... 521/64 |
| 6,426,373 B1 | * | 7/2002 | Stange et al. ............. 523/116 |
| 6,455,608 B1 | * | 9/2002 | Jia et al. .............. 523/115 |
| 6,500,004 B2 | * | 12/2002 | Jensen et al. ............ 433/228.1 |
| 6,503,958 B2 | * | 1/2003 | Hughes et al. .............. 521/64 |
| 6,506,816 B1 | * | 1/2003 | Ario et al. .............. 523/116 |
| 6,767,936 B2 | * | 7/2004 | Walz et al. .............. 523/105 |
| 2003/0114554 A1 | * | 6/2003 | Ario et al. .............. 523/116 |
| 2003/0199605 A1 | * | 10/2003 | Fischer .............. 523/116 |

FOREIGN PATENT DOCUMENTS

| | | |
|---|---|---|
| DE | 2 211 128 | 3/1973 |
| DE | 23 16 603 C3 | 4/1973 |
| DE | 3412650 A1 | 4/1984 |
| DE | 37 43 198 A1 | 12/1987 |
| DE | 38 56 261 T2 | 3/1988 |
| DE | 690 04 245 T2 | 12/1990 |
| DE | 691 01 702 T2 | 2/1991 |
| DE | 692 14 287 T2 | 5/1992 |
| DE | 692 18 202 T2 | 5/1992 |
| DE | 694 07 573 T2 | 1/1994 |
| DE | 694 22 069 T2 | 2/1994 |
| DE | 196 48 282 A1 | 11/1996 |
| EP | 0 394 792 A1 | 4/1990 |
| WO | WO 93/12759 | 7/1993 |
| WO | WO 95/27008 | 10/1995 |

OTHER PUBLICATIONS

Kitoh et al., "Adhesive Monomers to Dental Carmics. II. Methacrylamide Derivatives Containing Carboxyl and Phenyl Groups for Effective Adhesion of Calcium Metaphosphate Ceramic," *J. Applied Polymer Sci.*, 51:2021–2025 (1994).

Kitoh et al., "Studies on Adhesive Monomers for Teeth. V. Influence of Substituents in Methacrylamide Derivatives," *J. Applied Polymer Sci.*, 39:103–108 (1990).

Kulicke, "Polymerisation von Acrylamiden und Methacrylamiden (Polymerization of Acrylamides and Methacrylamides)," *Methoden der Organischen Chemie* (Houben-Weyl), vol. E20/2, G. Thieme–Verlag, Stuttgart–New York pp. 1176ff. (1987).

Ferruti et al., "Recent Results on Functional Polymers and Macromonomers of Interest as Biomaterials or for Biomaterial Modification," *Biomaterials*, 15: 1235–1241 (1994).

* cited by examiner

*Primary Examiner*—P. Hampton Hightower
(74) *Attorney, Agent, or Firm*—Nixon Peabody LLP

(57) ABSTRACT

Dental material containing an amide of the general formula $BX_n$ in which B stands for a hydrocarbon radical with 1 to 5 carbon atoms, which can contain one or more of the groups O, S, NH, CO—NH, O—CO—NH and/or NH—CO—NH, and which is substituted n times with the group X, X stands for the group

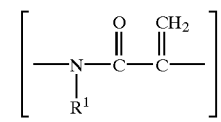

which is bound via the nitrogen atom or via C-2 to the radical B, the bond site not connected to B carrying a radical $R^2$, $R^1$ being hydrogen, an alkyl group with 1 to 20 carbon atoms or a phenyl radical, two or more radicals X being able to share a radical $R^1$ and $R^1$ also being able to be a constituent of the radical B, $R^2$ being hydrogen, an alkyl group with 1 to 20 carbon atoms or a phenyl radical, and n being a number from 2 to 5.

16 Claims, No Drawings

DENTAL MATERIALS BASED ON POLYFUNCTIONAL AMIDES

This application claims the benefit of U.S. Provisional Patent Application No. 60/289,097, filed May 7, 2001, which is herein incorporated by reference in its entirety.

The present invention relates to dental materials based on polyfunctional polymerizable amides.

Monofunctional amides of acrylic or methacrylic acid are used in various fields of dental medicine Thus GB 1,039,750 discloses mixtures of methyl methacrylate and acryl- or methacrylamide, the amides containing a free hydroxyl or ether group. Compounds with at least two olefinically polymerizable double bonds, such as e.g. glycoldiacrylate, divinylbenzene and glycerol tri(meth)acrylate, are used as cross-linkers. The mixtures are said to be particularly suitable for the preparation of dental prostheses.

Denture adhesives based on mixed polymers of acrylamides are known from DE 23 16 603, U.S. Pat. No. 3,926,870 and U.S. Pat. No. 5,011,868.

U.S. Pat. No. 3,660,343 discloses dental adhesives and filling materials which contain a thermally curable epoxy resin and N-3-oxohydrocarbon-substituted acrylamide.

(Meth)acrylic acid esters and (meth)acrylic acid amides containing formylpiperazine groups are known from EP 0 394 792 A1 which are said to be suitable for the preparation of adhesives and filling materials for the dental field.

Kitoh et al., J. Appl. Polym. Sci. 39 (1990) 103 and J. Appl. Polym. Sci. 51 (1994) 2021 investigated the influence of N-substituents on the adhesivity of methacrylamides to enamel and dental ceramics.

Furthermore, monofunctional acryl- and methacrylamides were used for the synthesis of polymeric precursors for substrates with bleaching effect (U.S. Pat. No. 5,560,749).

Products which are accessible through cross-linking copolymerization of acrylamides with bis-[acryloylamino]-methane can absorb many times their own weight of water and are used industrially as superabsorbers, for example for soil improvement and stabilization, for the preparation of incontinence articles or as stationary phase in electrophoresis (W. M. Kulicke, Polymerisation von Acrylamiden und Methacrylamiden [Polymerization of Acrylamides and Methacrylamides], in: Methoden der organischen Chemie (Houben-Weyl), vol. E20/2, G. Thieme-Verlag, Stuttgart-New York 1987, 1176ff.).

WO 95/27008 discloses auxiliaries for paper manufacture which are prepared by reacting a polyamine with a cross-linking agent such as for example bis(meth)acrylamide in an aqueous polyol solution.

The use of polyfunctional (meth)acrylamides for the preparation of dental materials has not been previously described.

The object of the invention is to provide dental materials with improved properties, i.e. in particular dental materials with a high hydrolysis resistance.

This object is achieved by dental materials which contain an amide of the general formula $BX_n$ in which B stands for a hydrocarbon radical with 1 to 50 carbon atoms, which can contain one or more of the groups O, S, NH, CO—NH, NH—CO, NH—CO—O, O—CO—NH and/or NH—CO—NH, and which is substituted n times with the group X.

X stands for the group

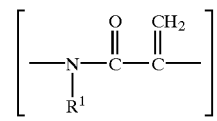

which is bound to the radical B via the nitrogen atom or via C-2, the bond site not connected to B carrying a radical $R^2$, $R^1$ is hydrogen, an alkyl group with 1 to 20 carbon atoms or a phenyl radical, two or more radicals X being able to share a radical $R^1$ and $R^1$ also being able to be a constituent of the radical B, $R^2$ is hydrogen, an alkyl group with 1 to 20 carbon atoms or a phenyl radical, and n is a number from 2 to 5.

The group X consists of N-substituted amide groups which are bound to the radical B via the amide nitrogen or via the carbon atom C-2. These two bond variants can be illustrated by the formulae (I) and (II).

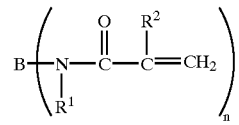

Formula I

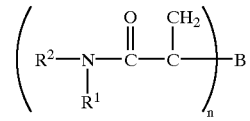

Formula II

Amides of formula I are preferred.

According to the invention, polyfunctional amides $BX_n$ are used for the preparation of dental materials, i.e. amides which contain at least two polymerizable groups X, preferably at least two (meth)acryl groups per molecule.

The radical $R^1$ can be a constituent of the group B so that the radical X is connected to B via two chemical single bonds. For example, the amide nitrogen or C-2 of the radical X can, together with $R^1$ and the atom of B to which they are bound, be part of a common cyclic or heterocyclic radical, the cyclic radical also being able to contain two or more amide nitrogens and two or more radicals $R^1$. In addition, two or more radicals X can share a common radical $R^1$.

In addition to the radicals X, B can carry one or more, for example 1 to 6 further substituents, in particular Cl, Br, quite particularly preferably OH and/or COOH. Preferably, B has 0 to 3 further substituents.

The radicals $R^1$ and $R^2$ can likewise, independently of each other, carry one or more, for example 1 to 3 substituents which are preferably chosen from Cl, Br, OH and/or COOH. Preferably $R^1$ and $R^2$ have 0 to 2 substituents.

Preferred meanings which can be chosen independently of each other for the variables of formula $BX_n$ are:

B=an n-valent linear or branched aliphatic $C_1$–$C_{50}$ radical, preferably $C_2$–$C_{50}$ radical, in which the carbon chain can be interrupted by O, S, NH, CO—NH, NH—CO, NH—CO—O, O—CO—NH or NH—CO—NH, an n-valent aromatic $C_6$–$C_{18}$ radical or an n-valent cycloaliphatic or heterocyclic $C_3$–$C_{18}$ radical, the radical being able to be substituted as above, $R_1, R_2$=independently of each other, hydrogen or an aliphatic C1–C20 alkyl or phenyl radical, the radicals being able to be substituted as indicated above, n=2 to 5.

Particularly preferred meanings, which can also be chosen independently of each other, for the variables of Formula $BX_n$ are:

B=(1) a saturated, linear or branched aliphatic group with 2 to 15, in particular 2 to 10 carbon atoms which can contain one or two of the groups S, NH and in particular O, NH—CO—O or O—CO—NH, (2) a cycloaliphatic group with 6 or 15 carbon atoms, (3) an aromatic or non-aromatic heterocyclic radical with 3 to 10 carbon atoms and 1 to 3 heteroatoms, (4) an aromatic radical with 6 to 12 carbon atoms or a combination of these radicals, $R_1$=hydrogen or a $C_1$ to $C_5$ alkyl group, in particular hydrogen or a $C_1$ to $C_3$ alkyl group, $R_2$=hydrogen or a $C_1$ to $C_5$ alkyl group, in particular hydrogen or a $C_1$ to $C_3$ alkyl group, n=2 or 3, in particular 2.

By combinations of meanings (1) to (4) are meant groups which for example are composed of several alicyclic or aromatic radicals and which are connected to each other directly or via O, S, NH, CO—NH, NH—CO, NH—CO—O, O—CO—NH and/or NH—CO—NH, e.g. -Ph-NH-Ph-, -cyclohexylene-cyclohexylene- and similar.

The amides of formula $BX_n$, are radically polymerizable and can be cured alone or preferably mixed with other polymerizable components in the presence of suitable polymerization initiators, e.g. thermally or by irradiation of light of the visible or UV range to form mechanically stable layers, preshaped parts or fillers.

The cross-linking density and thus the mechanical properties of the cured materials, such as E-modulus or strength, can be set selectively through the number of polymerizable groups of the multifunctional amides $BX_n$. Moreover, the solubility, functionality and reactivity of the multifunctional amides $Bx_n$ can be varied through the type of the organic basic structure B, through the substituents optionally also present as well as through the type and number of the substituents at the amide groups. For example, relatively flexible materials are obtained when using long-chained groups B whereas short-chained groups B tend more to lead to rigid and hard materials. The reactivity of the monomers, and in addition the achievable cross-linking density of the cured materials, increases with the number of polymerizable groups. The water-solubility of the amides $BX_n$ can be increased through OH and/or COOH substituents. COOH groups can in addition, through interaction with $Ca^{2+}$ ions, improve the adhesion of the materials to the enamel.

The amides $BX_n$ are soluble in water, alcohol, i.e. in particular methanol and ethanol, and in mixtures of these solvents and are characterized above all by a high hydrolysis stability in the presence of strong acids. They are particularly suitable for the preparation of dental coating materials, cements, filling materials and in particular adhesives.

The preferred multifunctional amides of the general formula I according to the invention can be prepared through the reaction of functional (meth)acrylic acid derivatives ($R^3$=Cl, O—CO—$CR_2$=$CH_2$, Oalkyl, OH) with primary ($R^1$=H) or secondary ($R^1$=alkyl or aryl) polyamines using the methods known from organic chemistry for the formation of amide bonds (cf. Methoden der Organischen Chemie, HOUBEN-WEYL vol. E5 1985, Georg Thieme Verlag p. 941ff.):

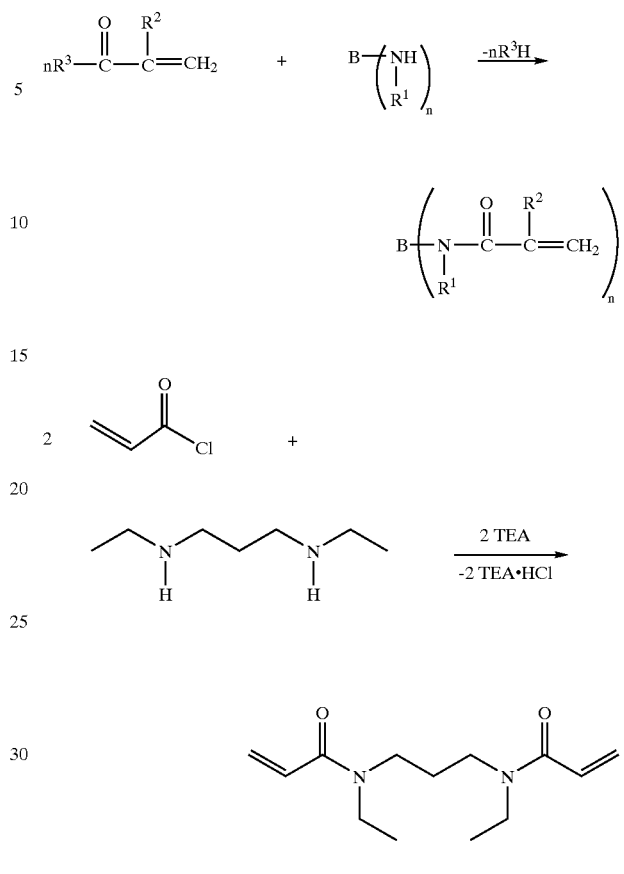

The acid chlorides ($R^3$=Cl) are preferably used which are reacted with the polyamine in the presence of an equimolar quantity of auxiliary base, e.g. triethylamine (TEA).

Concrete example:

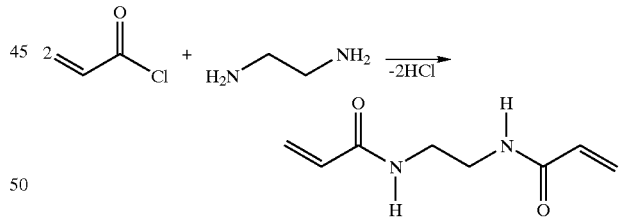

Advantageously, the polyamines can themselves also be used as acid captors (excess) as the corresponding hydrochlorides are very difficultly soluble and can thus be easily separated out of the reaction mixture (J. A. Helpern, Synth. Comm. 10 (1980) 569).

A further possibility for the synthesis of polyfunctional (meth)acrylamides is the reaction of N-(hydroxyalkyl)-(meth)acrylamides with polyisocyanates which leads to a link via hydrolysis-stable urethane bonds. The N-(hydroxyalkyl)-(meth)acrylamides required as starting compounds can be obtained from reactive (meth)acrylic compounds ($R^3$=Cl, O—CO—$CR_2$=$CH_2$, O-alkyl) through reaction with amino alcohols (cf. e.g. DE 3,412,650):

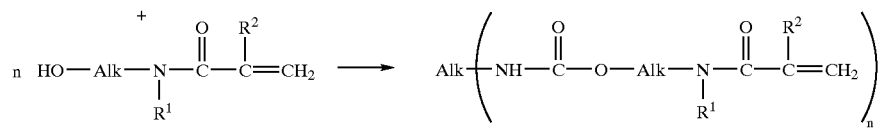

Concrete example:

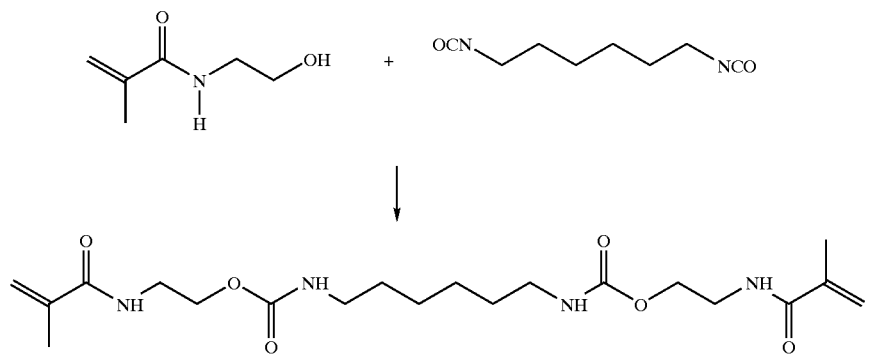

The amides of formula II according to the invention can be obtained e.g. through reaction of acrylic acid esters with aldehydes (D. Basavaiah, P. D. Rao, R. S. Hyma, Tetrahedron 56 (1996) 8001). Thus the reaction of acrylic acid esters with formaldehyde or primary aldehydes leads to α-hydroxymethacrylates which can be reacted with polyfunctional electrophilic reagents to form the corresponding polyfunctional methacrylates. By using polyfunctional aldehydes or formaldehyde in the case of acrylate excess, polyfunctional (meth)acrylic acid esters can also be obtained directly. The exchange of the esters for the amide function can take place either through aminolysis or through hydrolysis of the ester and subsequent condensation with amines in the Formula II

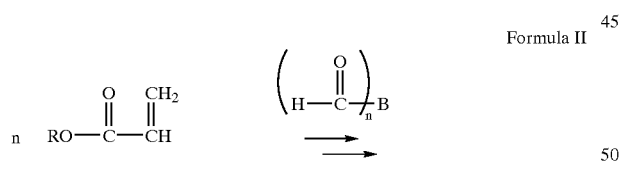

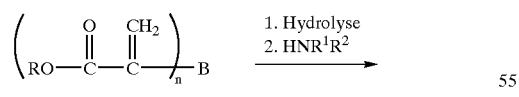

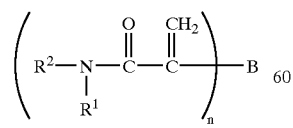

Carbodiimides or phosphorus oxychloride can be used as condensation agent for the amidation (Houben-Weyl; Stuttgart 1974; Georg Thieme Verlag 4$^{th}$ ed. vol. 15/2 Peptide; p. 103ff and 232ff).

Concrete example:

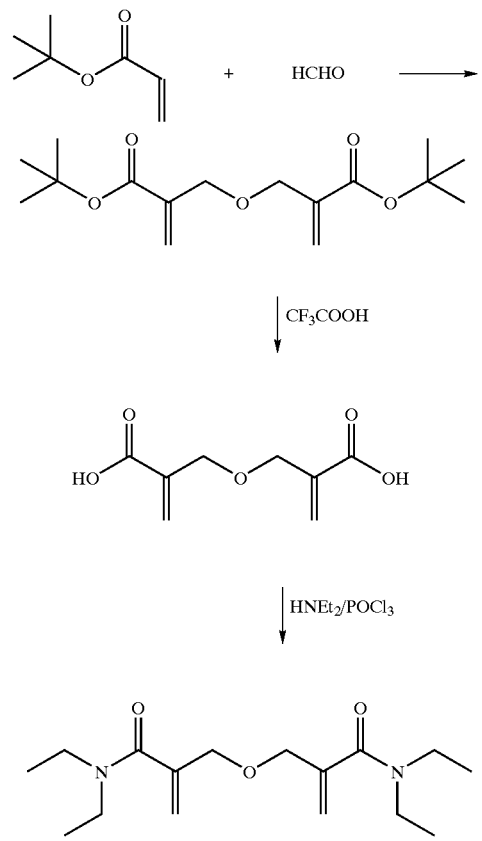

Concrete examples of the multifunctional (meth) acrylamides of the formulae (I) and (II) according to the invention are:

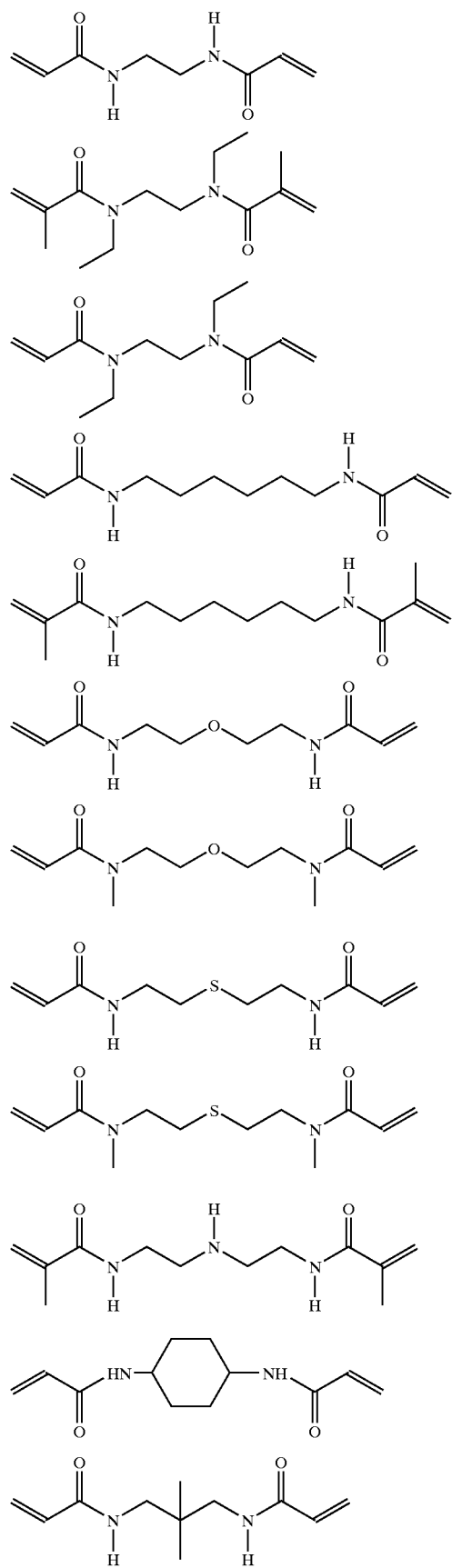
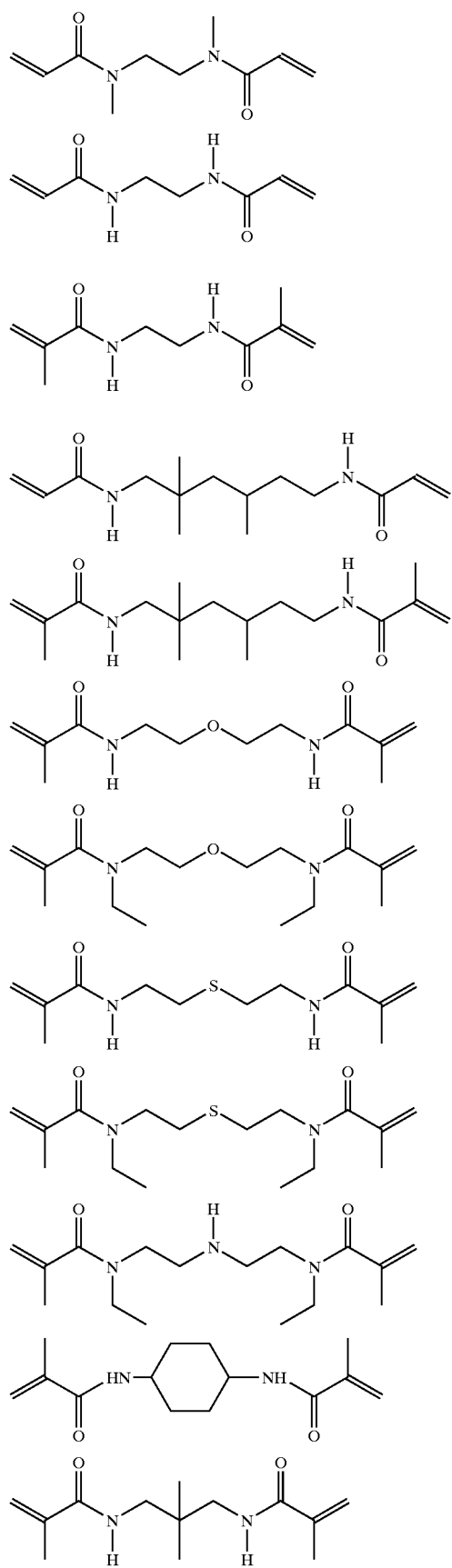

-continued

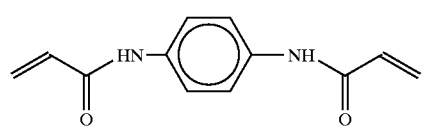
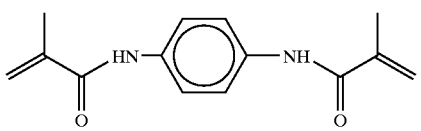
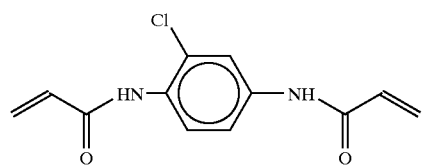
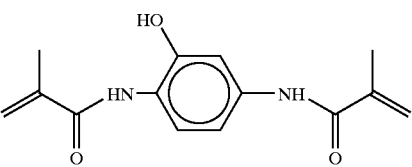
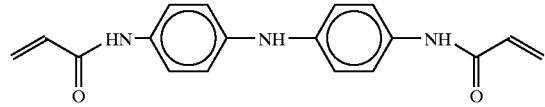
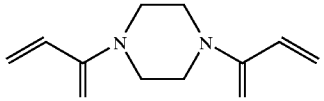
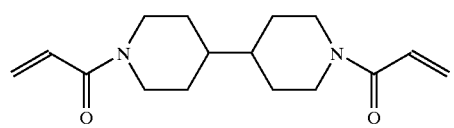
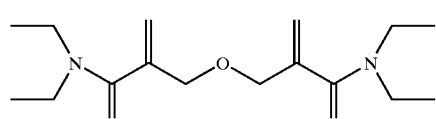
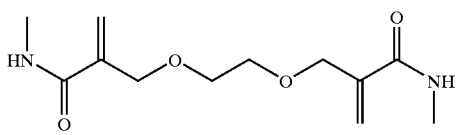
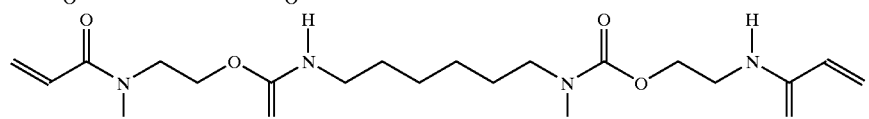
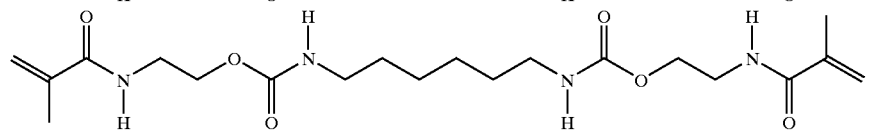
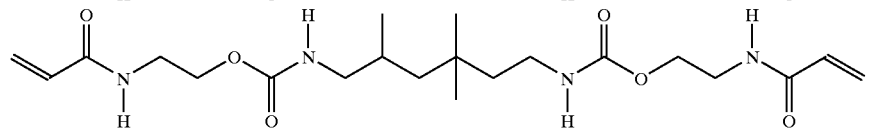
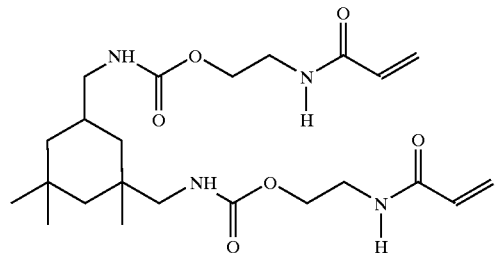

To prepare dental materials, the multifunctional amides $BX_n$ are mixed with a polymerization initiator and optionally further binders curable by radical polymerization, solvents, fillers and further additives.

The exact composition of the materials depends on the intended use. Adhesives preferably contain, in addition to at least one amide of the formula $BX_n$, polymerization initiator, at least one acidic polymerizable monomer and solvent.

Cements preferably contain, in addition to at least one amide of the formula $BX_n$, polymerization initiator, at least one acidic polymerizable monomer and filler.

Coating materials preferably contain, in addition to at least one amide of the formula $BX_n$, polymerization initiator, and solvent and filling materials, at least one amide of the formula $BX_n$, polymerization initiators and filler.

In each case, the quantity of the amide or amides $BX_n$ relative to the overall mass of the dental material is preferably at least 1 wt.-%, in particular at least 5 wt.-%.

All binders curable by polymerization, in particular ethylenically unsaturated, polymerizable monomers (acidic and non-acidic) such as monofunctional or polyfunctional (meth)acrylates and (meth)acrylamides which can be used alone or in mixtures are suitable as organic binders. Monofunctional monomers contain one, polyfunctional monomers two polymerizable groups. The binder preferably contains no amines with two or more amino groups.

Mono(meth)acrylamides and mono(meth)acrylates, e.g. acrylamide, methacrylamide, N-ethylacrylamide, methyl-, ethyl-, butyl-, benzyl-, furfuryl- or phenyl(meth)acrylate can be considered as preferred radically polymerizable monofunctional monomers.

Preferred polyfunctional monomers are the known polyfunctional acrylates or methacrylates such as e.g. bisphenol-A-di(meth)acrylate, bis-GMA (an addition product from methacrylic acid and bisphenol-A-diglycidyl ether), UDMA (an addition product from 2-hydroxyethyl methacrylate and 2,2,4-hexamthylene dilsocyanate), di-, tri- or tetraethylene glycol di(meth)acrylate, decanediol di(methacrylate), trimethylolpropane tri(meth)acrylate, pentaerythritol tetra(meth) acrylate as well as butanediol di(meth)acrylate, 1,10-decanediol di(meth)acrylate or 1,12-dodecanediol di(meth) acrylate.

The multifunctional amides $BX_n$ are particularly suitable as cross-linkers for strongly acidic polymerizable monomers which are often used in adhesives. These include in particular phosphoric acid ester methacrylates such as e.g. 2-(methacryloyloxyethyl)-dihydrogenphosphate, di-(2-methacryloyloxyethyl hydrogenphosphate or dipentaerythritol pentamethacryloyloxy dihydrogenphosphate (cf. N. Nakabayashi, P. D. Pashley, Hybridization of dental hard tissues, Quintess. Publ. Tokyo etc. 1998, 9 ff). Particularly preferred are hydrolysis-stable acrylphosphonic acids such as e.g. 2-[3-(dihydroxyphosphoryl)-oxa-propyl] acrylic acid ethyl ester or 1,2-bis[1-dihydroxyphosphoryl]-1-[2-methylene-3-ylpropanoic acid ethyl ester)oxy]methyl]-benzene which are described in DE 197,46,708 C2. To distinguish between acidic and non-acidic monomers, the term "polymerizable monomer" is used for non-acidic components, the term "polymerizable binder" includes acidic and non-acidic substances.

When using further polymerizable monomers (acidic and non-acidic), the quantity of the amide or amides $BX_n$ relative to the sum of the masses of the amide or amides $BX_n$ and of the polymerizable monomers is preferably greater than 3 wt.-%, particularly preferably greater than 10 wt.-%.

The curing of the compositions can take place, depending on the type of polymerization initiator used, by thermal, photochemical or redox-induced radical polymerization.

Preferred examples of thermal initiators are the known peroxides, such as e.g. dibenzoyl peroxide, dilauryl peroxide, tert.-butyl peroctoate or tert.-butylperbenzoate as well as azobisisobutyroethyl ester, azobisisobutyronitrile, azobis-(2-methylpropionamidine) dihydrochloride benzopinacol or 2,2-dimethlybenzopinacol.

Preferred photoinitiators are benzophenone, benzoin as well as their derivatives or α-diketones or their derivatives such as 9,10-phenanthrenoquinone, diacetyl or 4,4-dichlorobenzil. Particularly preferably, camphorquinone and 2,2-dimethoxy-2-phenylacetophenone and particularly preferably α-diketones are used in combination with amines as reduction agent such as e.g. 4-(N,N-dimethylamino)-benzoic acid ester, N,N-diemethylaminoethyl methacrylate, N,N-dimethyl-sym.-xylidine or triethanolamine. In addition, acylphosphines, such as e.g. 2,4,6-trimethylbenzoyldiphenyl- or bis(2,6-dichlorobenzoyl)-4-N-propylphenyl phosphinic oxide are particularly suitable.

Redox initiator combinations, such as e.g. combinations of benzoyl or lauryl peroxide with N,N-dimethyl-sym. xylidine or N,N-dimethyl-p-toluidine, are used as initiators for the polymerization carried out at room temperature.

Compositions which contain an initiator for the photopolymerization are preferred.

Polar solvents, such as water, ethanol, acetone, acetonitrile or mixtures of these solvents can preferably be used as solvent for the multifunctional amides $BX_n$.

Furthermore, the compositions used according to the invention can be filled with inorganic particles or fibres to improve the mechanical properties. Preferred inorganic particulate fillers are amorphous spherical materials based on oxides, such as $ZrO_2$ and $TiO_2$ or mixed oxides of $SiO_2$, $ZrO_2$ and/or $TiO_2$ with a mean average particle size of 0.005 to 2.0 μm, preferably 0.1 to 1 μm, such as are disclosed for example in DE-PS 32 47 800, nanoparticulate or microfine fillers, such as pyrogenic silicica acid or precipitated silicica as well as macro- or minifillers, such as quartz, glass ceramic or glass powder with an average particle size of 0.01 to 20 μm, preferably 0.01 to 5 μm as well as x-ray opaque fillers, such as ytterbium trifluoride. By minifillers are meant fillers with a particle size of 0.5 to 1.5 μm and, by macrofillers, fillers with a particle size of 10 to 20 μm.

Optionally, the compositions used according to the invention can contain further additives, such as e.g. colorants (pigments or dyes), stabilizers, aromatics, microbicidal active ingredients, plasticizers or UV-absorbers.

A particularly preferred dental material contains, in each case relative to the overall mass of the dental material:

(a) 1 to 90 wt.-%, in particular 5 to 50 wt.-%, quite particularly preferably 8 to 40 wt.-% amide of the formula $BX_n$,
(b) 0.1 to 5.0 wt.-%, in particular 0.2 to 2.0 wt.-% polymerization initiator,
(c) 0 to 70 wt.-%, in particular 0 to 50 wt.-% polymerizable monomer,
(d) 0 to 70 wt.-%, preferably 0 to 50 wt.-%, particularly preferably 0 to 40 wt.-% acidic monomer,
(e) 0 to 70 wt.-%, in particular 0 to 50 wt.-%, filler, and/or
(f) 0 to 70 wt.-%, in particular 0 to 50 wt.-% solvent.

Compositions which contain at least one polyfunctional polymerizable monomer as component (c) are preferred, the proportion of the polyfunctional monomer or monomers in the component (c) according to a particularly preferred version being at least 50 wt.-% relative to the mass of the component (c).

This composition can be further optimized for particular uses. Thus a dental material which is suitable in particular as an adhesive preferably contains, in each case relative to the overall mass of the dental material:

(a) 5 to 40 wt.-% amide of the formula $BX_n$,
(b) 0.2 to 2.0 wt.-% polymerization initiator,
(c) 0 to 40 wt.-% polymerizable monomer,
(d) 5 to 40 wt.-% acidic monomer and
(f) 2 to 50 wt.-% solvent.

A dental material which is suitable in particular as a dental cement preferably contains, in each case relative to the overall mass of the dental material:

(a) 5 to 20 wt.-% amide of the formula $BX_n$,
(b) 0.2 to 2.0 wt.-% polymerization initiator,
(c) 0 to 20 wt.-% polymerizable monomer,
(d) 2 to 20 wt.-% acidic monomer and
(e) 5 to 60 wt.-% filler.

A dental material which is suitable in particular as a dental coating material preferably contains, in each case relative to the overall mass of the dental material:
(a) 5 to 40 wt.-% amide of the formula $BX_n$,
(b) 0.2 to 2.0 wt.-% polymerization initiator,
(c) 0 to 50 wt.-% polymerizable monomer and
(f) 5 to 50 wt.-% solvent.

A dental material which is suitable in particular as a dental filling material preferably contains, in each case relative to the overall mass of the dental material:
(a) 5 to 20 wt.-% amide of the formula $BX_n$,
(b) 0.2 to 2.0 wt.-% polymerization initiator,
(c) 0 to 30 wt.-% polymerizable monomer and
(e) 10 to 70 wt.-% filler.

The dental materials according to the invention are characterized in the cured and uncured state by a high hydrolysis-stability in particular also in the presence of acidic compounds, and are also storage-stable in the uncured state, too.

The invention is explained in more detail in the following with the help of examples. Unless otherwise stated, all percentages are wt.-%.

EXAMPLE 1

Synthesis of ethylene bisacrylamide (1) (J. A. Helpern, Synth. Comm. 10 (1980) 569)

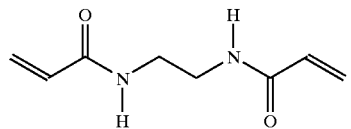

90.5 g (1.0 mol) acrylic acid chloride and 16 mg hydroquinone monomethyl ether (MEHQ, stabilizer) were dissolved in 3 l methylene chloride in a 6-l sulphonation flask and cooled to 0° C. Then, a solution of 60.1 g (1.0 mol) ethylenediamine in 2 l methylene chloride was added dropwise accompanied by stirring so that the temperature remained between 0–5° C. After 6 hours stirring, the mixture was allowed to warm up to room temperature, the precipitate formed was then filtered off and the solid washed with 1 l acetonitrile. The filtrate and the washing solution were combined and concentrated under vacuum to give a thick suspension. The solid was then filtered off, dried and dissolved and recrystallized from approx. 1.3 l acetone. 42.5 g (56% yield) of a white solid with a melting point of 142–145° C. were obtained.

$^1$H-NMR (400 MHz, CDCl$_3$): δ=3.15–3.30 (m; 4H, CH$_2$CH$_2$), 5.55–5.65 and 6.02–6.28 (m; 2H+4H, CH=CH$_2$) ppm.

EXAMPLE 2

Synthesis of N,N'-diethyl-1,3-propylene-bis-acrylamide (2)

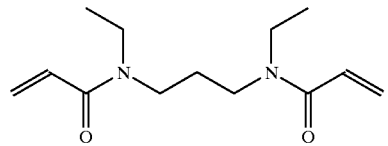

36.3 g (0.40 mol) acrylic acid chloride and 4 mg MEHQ were dissolved in 1.2 l acetonitrile in a 2.5-l sulphonation flask and cooled to −5° C. Then, a solution of 46.9 g (0.36 mol) N,N'-diethylpropylenediamine in 1.2 l acetonitrile was added dropwise accompanied by stirring so that the temperature remained between −5 and 0° C. After 1.5 h, the mixture was allowed to warm up to room temperature and stirred for a further 4 h, the precipitate formed was then filtered off and washed with 0.5 l acetonitrile. The acetonitrile phases were combined and concentrated under vacuum (10 mbar, 40° C.). The raw product was taken up in 150 ml acetone, filtered through a frit with 50 g silica gel 60 and concentrated again. After repeating this process, 32.7 g (76% yield) of a light yellow liquid (η (23° C.)=270 mPa·s) remained.

$^1$H-NMR (400 MHz, DMSO-d$_6$): δ=1.10–1.25 (m; 6H, CH$_3$), 1.80–1.92 (m; 2H, CH$_2$C$\underline{H}_2$—CH$_2$), 3.35–3.61 (m; 8H, CH$_2$N), 5.63–5.77, 6.28–6.42 and 6.47–6.66 (m; 3×2H, CH=CH$_2$) ppm.

EXAMPLE 3

Synthesis of bis[2-(2-methyl-acrylamino)-ethoxycarbonyl]-hexamethylenediamine (3)

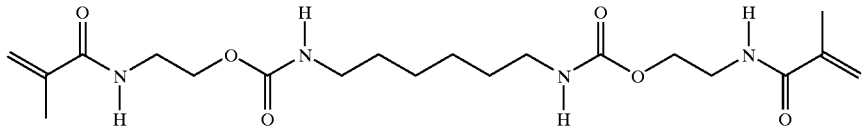

6.44 g (49.9 mmol) N-(2-hydroxyethyl)-methacrylamide and 12 mg MEHQ were dissolved in 25 ml anhydrous methylene chloride. After adding 2 drops dibutyltindioctanoate as catalyst (Metatin 812), 4.19 g (24.9 mmol) hexamethylene diisocyanate were added dropwise accompanied by cooling so that the temperature remained at approx. 5° C. Then stirring was carried out for approx. 4 d at room temperature, the solvent removed and the solid raw product dissolved and recrystallized twice from anhydrous ethanol. 4.8 g (45% yield) of a colourless crystalline solid (m.p.: 154–155° C. accompanied by polymerization) were obtained.

$^1$H-NMR (400 MHz, DMSO-d$_6$): δ=1.22 (br. s; 4 H, CH$_2$CH$_2$C$\underline{H}_2$C$\underline{H}_2$CH$_2$CH$_2$), 1.35 (br. s, 4H, CH$_2$C$\underline{H}_2$CH$_2$C$\underline{H}_2$CH$_2$), 1.84 (s; 6H, CH$_3$), 2.91–2.96, (m; 4H, CH$_2$NHCOO), 3.28–3.34 (m; 4H, C$\underline{H}_2$NHCOC=C), 3.92–4.00 (m; 4H, CH$_2$O), 5.32, 5.66 (s; 4H, CH$_2$=), 6.8, 7.11 and 7.98 (br.; 0.25H+1.75H+2H, NH, H/D exchange).

EXAMPLE 4

Synthesis of N,N'-(dimethyl)-ethylenebisacrylamide (4)

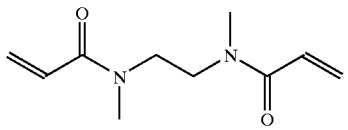

36.2 g (0.40 mol) acrylic acid chloride and 16 mg MEHQ were dissolved in 600 ml methylene chloride in a 1.5-l sulphonation flask and cooled to −5° C. Then, a mixture of 17.6 g (0.20 mol) N,N'-dimethylethylenediamine, 40.8 g (0.40 mol) triethylamine and 400 ml methylene chloride was added dropwise accompanied by stirring so that the temperature remained between −5 and 0° C. After 1.5 h stirring, the mixture was allowed to warm up to room temperature, stirred overnight, the precipitate formed was filtered off and the filtrate concentrated under vacuum. The raw product was taken up in 150 ml acetone, filtered through a frit with 50 g silica gel 60 and concentrated again. After repeating this process, 30.1 g (77% yield) of a light yellow liquid remained.

$^1$H-NMR (400 MHz, CDCl$_3$): δ=3.10 and 3.14 (s; 2×3H, CH$_3$), 3.54–3.67 (2m; 4H, CH$_2$N), 5.68, 6.35 and 6.56 (m; 3×2H, CH═CH$_2$) ppm.

EXAMPLE 5

Synthesis of 2,2,4-trimethylhexamethylene-1,6-bismethacrylamide (5)

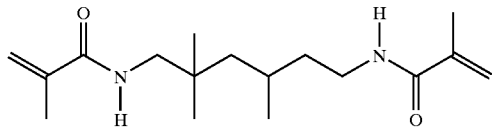

142.0 g (0.90 mol) 2,2,4-trimethylhexamethylenediamine in 2 l acetonitrile were added dropwise accompanied by cooling with ice to a solution of 104.5 g (1.0 mol) methacrylic acid chloride and 20 mg phenothiazine in 3 l acetonitrile. After 16 h stirring at room temperature, the white suspension formed was filtered off. The filtrate was reduced on the rotary evaporator accompanied by the introduction of dry air. The remaining product was dissolved in 1 l methylene chloride and washed several times with 1 l 2N HCl each time, diamine no longer being detectable by thin-layer chromatography (TLC). After the further washing with 500 ml 2N sodium hydroxide solution and 500 ml salt water, the methylene chloride solution was dried over sodium sulphate and the solvent completely distilled off on the rotary evaporator at 40° C. 124.5 g (94% yield) of a clear viscous liquid remained.

$^1$H-NMR (400 MHz, CDCl$_3$): δ=0.88–0.97 (m; 9H, (CH$_3$)$_2$ C+C$\underline{H}_3$—CH), 1.46–1.69 (m; 5H, CH$_2$CHCH$_2$), 1.95 (s; 6H, ═C—CH$_3$), 3.25–3.32 (m; 4H, CH$_2$N), 5.32 and 5.69 (s; 2×2H, ═CH$_2$) and 6.50–6.71 (br; 2H, NH) ppm.

EXAMPLE 6

Synthesis of 3,3'-oxybis(2-methylene propionic acid diethylamide) (6)

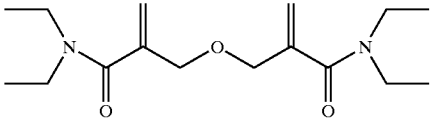

37.2 g (0.20 mol) 3,3'-oxybis(2-methylene propionic acid) were dissolved in 1.75 l tetrahydrofuran (THF) in a 2.5-l sulphonation flask and cooled to −20° C. Then, 29.2 g (0.40 mol) diethylamine were added dropwise accompanied by stirring so that the temperature did not exceed −15° C. Subsequently, at −15° C., firstly 61.2 g (0.40 mol) phosphoryl chloride and then 121.2 g (1.2 mol) triethylamine were added dropwise and the mixture stirred for a further 6 hours. After standing overnight at room temperature, the precipitate formed was filtered off and washed with 250 ml THF. The combined THF phases were concentrated under vacuum and mixed with 200 ml water. The clear solution produced was extracted several times with 100 ml methylene chloride each time. Subsequently, the extract was washed with 2N NaOH, dried over anhydrous sodium sulphate and concentrated by evaporation. The liquid raw product was distilled under fine vacuum, and 18.5 g (31% yield) of a light-yellow oil (η (23° C.)=170 mPa·s) were isolated at 148° C. (0.04 mbar).

$^1$H-NMR (400 MHz, CDCl$_3$): δ=1.16 (t; 12H, CH$_3$), 3.42 (q; 8H, CH$_2$N), 4.23 (s; 4H, OCH$_2$═), 5.19 and 5.38 (m; 2×2H, ═CH$_2$) ppm.

EXAMPLE 7

Radical Polymerization of Amides 1 to 5

Homogeneous mixtures each comprised of 30% of one of the amides of examples 1 to 5 or glycerine dimethacrylate as comparison example, 20% of water, 49% of ethanol and 1% of 2,2 '-azobis-(2-methylpropionamidine)-dihydrochloride (initiator), were prepared in Schlenk flasks and deaerated by passing through argon. The polymerization mixtures were then heated to 65° C. in a thermostat. The time which elapsed until a three-dimensional stable gel formed was measured (gel time).

| Monomer | Gel time [minutes] | Hydrolysis stability[a] |
|---|---|---|
| Example 1 | 1 | + |
| Example 2 | 4 | + |
| Example 3 | 6 | + |
| Example 4 | 9 | + |
| Example 5 | 7 | + |
| Glycerine dimethacrylate (comparison example) | 4 | − |

[a]To establish hydrolysis stability, a 20 wt.-% solution of the relevant monomer was stored in a 1:1:1 mixture of water, ethanol and 10% phosphoric acid at 37° C. After 4 weeks, the solution was examined by $^1$H-NMR spectroscopy.
+: no hydrolysis of the monomer was observed
−: the polymer was completely degraded The polymerization tests show that the amides BX$_2$ have a variable polymerizability. The bisacrylamide from example 1 is clearly more reactive, the amide from example 2 equally reactive and the bismethacrylamide e.g. from example 4 less reactive than glycerine dimethacrylate. The gel time serves as a measure of the polymerizability. This is the time which elapses until a three-dimensional polymer network, i.e. a so-called gel, has formed from a solution containing cross-linker and monomer. The shorter the gel time, the more reactive the corresponding cross-linking monomer. Glycerine dimethacrylate was chosen as comparison compound as it is the only conventional cross-linking monomer which has both a degree of water solubility and a very good radical polymerizability.

A major advantage of the amides according to the invention is to be seen in their hydrolysis stability. Aqueous solutions of the amides are thus also storage-stable in the presence of acidic compounds. As a linking of the monomer components via covalent C—C single bonds takes place on polymerization, this also applies to the corresponding polymers. On the other hand, glycerine dimethacrylate is completely split to form glycerine and methacrylic acid in the presence of phosphoric acid.

EXAMPLE 8

Dentine adhesive containing N,N'-(diethyl)-1,3-propylene-bis-acrylamide (2)

To investigate dentine adhesion on bovine teeth dentine, an adhesive of the following composition (values in wt.-%) was prepared:

| | |
|---|---|
| Strongly acidic adhesive monomer[a]: | 11.1% |
| Glycerine dimethacrylate: | 11.0% |
| 2-hydroxyethyl methacrylate: | 20.0% |
| Ethanol: | 24.0% |
| Bisacrylamide 2: | 33.1% |
| Photoinitiator: | 0.8% |

[a] 2-[3-(dihydroxyphosphoryl)-2-oxa-butyl]-acrylic acid ethyl ester (cf. DE 197 46 708 C2)

Bovine teeth were embedded in a plastic cylinder such that the dentine and the plastic were located on one level. The free surface of the tooth was treated with 37% phosphoric acid and rinsed thoroughly with water after 15 seconds etching. The dentinal tubuli were opened by the acid etching. Then a layer of adhesive of the above composition was applied with a small brush, the treated surface blasted briefly with an air jet to remove the solvent and illuminated for 40 s by a halogen lamp with light of a wavelength of 390 to 500 nm (Astralis 7, Vivadent). A composite cylinder made of Tetric® Ceram (Vivadent, 16 wt.-% polymerizable monomer, 0.5 wt.-% photoinitiator and stabilizer, 83.5 wt.-% filler) was polymerized onto the cured adhesive layer in two layers of 1–2 mm each. The thus-prepared teeth were then stored in water for 24 hours at 37° C. and the shearing adhesive strength measured. A value of 15.4 MPa was measured.

What is claimed is:

1. Dental material containing an amide of the general formula $BX_n$ in which

B is a hydrocarbon radical with 2 to 50 carbon atoms which can contain one or more of the groups O, S, NH, CO—NH, and/or NH—CO—NH, and which is substituted n times with the group X, X is the group $$\left[ -\underset{R^1}{N} - \overset{O}{\underset{\|}{C}} - \overset{CH_2}{\underset{\|}{C}} - \right]$$

which is bound to the radical B via the nitrogen atom or via C-2, the bond site not connected to B carrying a radical $R^2$, $R^1$ is hydrogen, an alkyl group with 1 to 20 carbon atoms or a phenyl radical, two or more radicals X being able to share a radical $R^1$ and $R^1$ also being able to be a constituent of the radical B, $R^2$ is hydrogen, an alkyl group with 1 to 20 carbon atoms or a phenyl radical, and n is a number from 2 to 5, and at least one acidic polymerizable monomer.

2. Dental material according to claim 1, wherein

B is a saturated, linear or branched aliphatic group with 2 to 15 carbon atoms which can contain one or two of the groups S, NH, O, NH—CO—O or O—CO—NH, for a cycloaliphatic group with 6 or 15 carbon atoms, an aromatic or non-aromatic heterocyclic radical with 3 to 10 carbon atoms and 1 to 3 heteroatoms, an aromatic radical with 6 to 12 carbon atoms or a combination of these radicals, $R^1$ is hydrogen or a $C_1$ to $C_5$ alkyl group, $R^2$ is hydrogen or a $C_1$ to $C_5$ alkyl group, n is 2 or 3.

3. Dental material according to claim 1, wherein B carries, in addition to the group X, one or more substituents which are chosen from Cl, Br, OH and/or COOH.

4. Dental material according to claim 1, wherein $R^1$ and/or $R^2$ are substituted once or several times, the substituent or substituents being chosen from Cl, Br, OH and/or COOH.

5. Dental material according to claim 1, wherein the material contains a polymerization initiator and optionally a polymerizable binder.

6. Dental material according to claim 5, wherein the material contains at least one acidic polymerizable monomer.

7. Dental material according to claim 5, wherein the material contains at least one ethylenically unsaturated polymerizable monomer.

8. Dental material according to claim 7, wherein the material contains a polyfunctional polymerizable monomer.

9. Dental material according to claim 5, wherein the quantity of the amide $BX_n$ relative to the sum of the masses of the amide $BX_n$ and other polymerizable monomers is more than 3 wt.-%.

10. Dental material according to claim 5, wherein the material contains an initiator for the photopolymerization.

11. Dental material according to claim 1, wherein the material contains filler.

12. Dental material according to claim 1, wherein the material contains at least 1 wt.-% of the amide $BX_n$ relative to the overall mass of the dental material.

13. Dental material according to claim 1, wherein the material contains (a) 1 to 90 wt.-% of the amide $BX_n$, (b) 0.1 to 5.0 wt.-% polymerization initiator, (c) 0 to 70 wt.-% polymerizable monomer (non-acidic),
(d) 0 to 70 wt.-% acidic polymerizable monomer,
(e) 0 to 70 wt.-% filler,
(f) 0 to 70 wt.-% solvent in each case relative to the overall mass of the dental material.

14. An amide of the general formula $BX_n$ in which

B is a hydrocarbon radical with 2 to 50 carbon atoms which can contain one or more of the groups O, S, NH, CO—NH, and/or NH—CO—NH, and which is substituted n times by the group X, X is the group

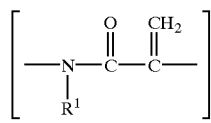

which is bound to the radical B via the nitrogen atom or via C-2, the bond site not connected to B carrying a radical $R^2$, $R^1$ is hydrogen, an alkyl group with 1 to 20 carbon atoms or a phenyl radical, two or more radicals X being able to share a radical $R^1$ and $R^1$ also being able to be a constituent of the radical B, $R^2$ is hydrogen, an alkyl group with 1 to 20 carbon atoms or a phenyl radical, and n is a number from 2 to 5, comprising a dental adhesive, coating material, filling material or dental cement.

15. Dental material according to claim 9, wherein the quantity of the amide $BX_n$ is more than 10 wt.-%.

16. Dental material according to claim 12, wherein the material contains at least 5 wt.-% of the amide $BX_n$.

* * * * *